United States Patent
Sun et al.

(10) Patent No.: US 9,912,340 B1
(45) Date of Patent: Mar. 6, 2018

(54) GENERATING GRADIENT WAVEFORM

(71) Applicant: Shenyang Neusoft Medical Systems Co., Ltd., Shenyang (CN)

(72) Inventors: Rong Sun, Shenyang (CN); Hongwei Wang, Shenyang (CN); Yan Wang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 0 days.

(21) Appl. No.: 15/697,371

(22) Filed: Sep. 6, 2017

(30) Foreign Application Priority Data

Sep. 7, 2016 (CN) .......................... 2016 1 0807641

(51) Int. Cl.
| | |
|---|---|
| *H03M 1/66* | (2006.01) |
| *H03M 1/06* | (2006.01) |
| *G01R 33/385* | (2006.01) |
| *G06T 15/20* | (2011.01) |
| *A61B 5/00* | (2006.01) |

(52) U.S. Cl.
CPC .............. *H03M 1/06* (2013.01); *A61B 5/0033* (2013.01); *G01R 33/385* (2013.01); *G06T 15/205* (2013.01); *H03M 1/66* (2013.01)

(58) Field of Classification Search
CPC ...... G06T 15/205; H03M 1/66; G01R 33/385; A61B 5/0033

USPC .............................................. 341/144, 1, 43
See application file for complete search history.

(56) References Cited

U.S. PATENT DOCUMENTS

| | | | | |
|---|---|---|---|---|
| 7,548,062 | B1 * | 6/2009 | Gurney ................ | G01R 33/561 324/307 |
| 7,791,338 | B2 * | 9/2010 | Kim ..................... | G01R 33/561 324/307 |
| 9,476,956 | B2 * | 10/2016 | Taniguchi .............. | A61B 5/055 |
| 9,664,765 | B2 * | 5/2017 | Hanada ............ | G01R 33/56518 |

* cited by examiner

*Primary Examiner* — Brian Young
(74) *Attorney, Agent, or Firm* — McCoy Russell LLP

(57) ABSTRACT

Methods of generating a gradient waveform, gradient waveform generators and magnetic resonance imaging systems are provided. In one aspect, a first digital value is obtained by quantizing and coding spatial position information of a voxel of a subject according to the number of preset quantization bits, wherein the number of the quantization bits are more than the number of allowed input bits for a DAC; a second digital value is determined to be inputted into the DAC according to the first digital value and the number of the allowed input bits for the DAC; a quantization error is determined according to the first digital value and the second digital value; an error accumulating value is updated by accumulating the quantization error to the error accumulation value; the second digital value corrected according to the error accumulation value; and the corrected second digital value is inputted into the DAC.

18 Claims, 4 Drawing Sheets

US 9,912,340 B1

GENERATING GRADIENT WAVEFORM

CROSS REFERENCE TO RELATED APPLICATIONS

This application claims priority to Chinese Patent Application No. 201610807641.7, entitled "Method, Apparatus for Improving DAC Output Waveform Accuracy, and Magnetic Resonance Imaging System," filed on Sep. 7, 2016, the entire contents of which are incorporated herein by reference for all purposes.

TECHNICAL FIELD

The present disclosure relates to generating a gradient waveform in a magnetic resonance imaging system.

BACKGROUND

In a magnetic resonance imaging system, it may be desirable to accurately locate a spatial position of a voxel of a subject, so as to obtain accurate image information. The magnetic resonance imaging system can generate a gradient waveform through a gradient waveform generator. And a gradient amplifier amplifies the gradient waveform to drive a three-dimensional gradient coil, so as to determine a spatial position of each voxel of a subject. Gradient waveform accuracy is regarded as one of many relevant factors for influencing spatial positioning accuracy.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Figure 1:
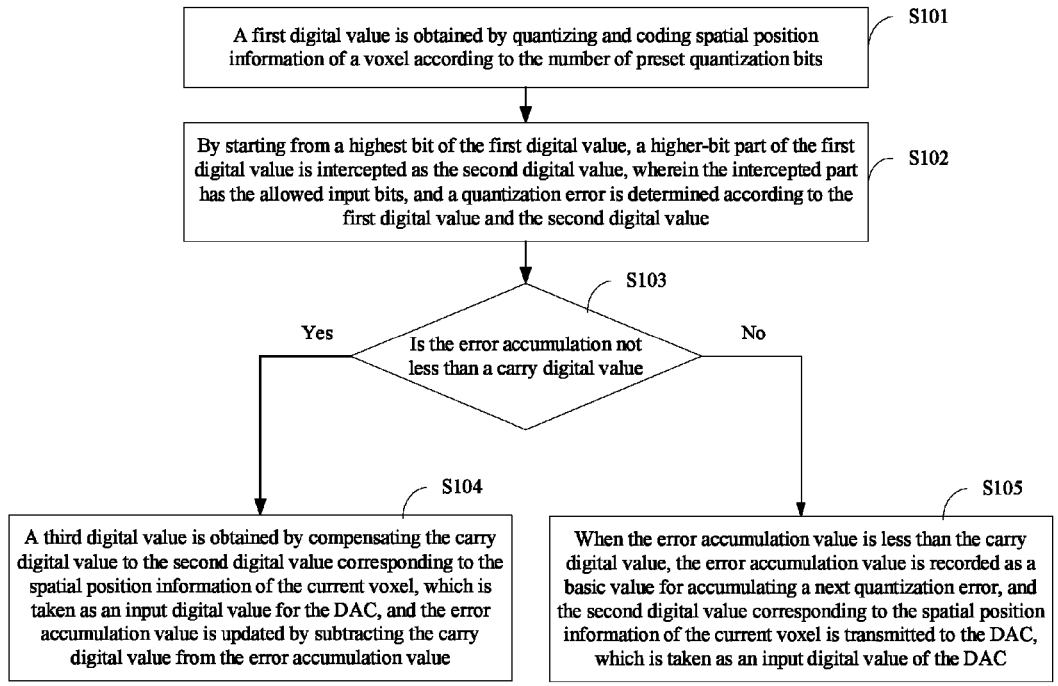
FIG. 1 is a flowchart illustrating a method of generating a gradient waveform according to an example of the present disclosure.

Embodiments will be described in detail herein, the examples of which are expressed in the drawings. When the following descriptions involve the drawings, like numerals in different drawings represent like or similar elements unless stated otherwise. The implementations described in the following examples do not represent all implementations consistent with the present disclosure. On the contrary, they are examples of a device and a method consistent with some aspects of the present disclosure as described in detail in the appended claims.

A magnetic resonance imaging system includes a three-dimensional gradient subsystem, a radio-frequency transmitting subsystem, and a radio-frequency receiving subsystem, where an input signal of the three-dimensional gradient subsystem is spatial position information of a voxel of a part to be examined of a subject, including information corresponding to a specific spatial position of the voxel in a field of view of a magnetic body cavity. The information corresponding to the spatial position is inputted into a gradient waveform generator in the three-dimensional gradient subsystem. The gradient waveform generator can generate three-dimensional gradient pulse signals. The three-dimensional gradient pulse signals include a slice-selection direction gradient signal, a frequency-coding gradient signal, and a phase-coding gradient signal. A gradient amplifier in the three-dimensional gradient subsystem amplifies the three-dimensional gradient pulse signals. And, a gradient coil in the three-dimensional gradient subsystem generates a three-dimensional gradient magnetic field based on the three-dimensional gradient pulse signals, where the three dimensional gradient magnetic field enables an image to have spatial information.

The magnetic resonance imaging system may perform digital coding for the information corresponding to the spatial position (i.e., spatial position information) of a voxel of a subject through a computer to obtain a digital value (generally in a binary form). The digital value is inputted into a Digital to Analog Converter (DAC) in the gradient waveform generator and converted into a gradient waveform by the DAC. A quantization error may be generated when quantizing and coding the spatial position information of the voxel of the subject, and the quantization error is reversely proportional to quantization bits. That is, the more the quantization bits are, the smaller the quantization error is. If the quantization error is too big, it is possible to cause that a spatial position of a voxel of a subject is not accurate, and there are image artifacts, etc.

To solve the problems recognized by the inventors above, the present disclosure provides a method of generating a gradient waveform, where the method of generating a gradient waveform can apply to a gradient waveform generator in a magnetic resonance imaging system in a way that a DAC in the gradient waveform generator can output a high-accuracy gradient waveform.

FIG. 1 is a flowchart illustrating a method of generating a gradient waveform according to an example of the present disclosure. The method includes procedures as follows.

At block S101, a first digital value is obtained by quantizing and coding spatial position information of a voxel according to the number of preset quantization bits, where the number of the quantization bits is more than the number of bits of a digital value allowed to be inputted into a DAC (hereinafter referred to as allowed input bits for the DAC).

In an example of the present disclosure, the collected spatial position information of a voxel may be quantized and coded according to the number of the preset quantization bits through a device with a digital coding function, e.g., a Central Processing Unit (CPU) of a computer and an Advanced Reduced Instruction-Set Computer (RISC) Machine and the like. It is in demand that the number of the preset quantization bits is more than the number of the allowed input bits for the DAC so as to guarantee accuracy for performing quantizing and coding, however, the specific number of the quantization bits is not limited in the present disclosures.

In an example, by using a CPU of a computer, the spatial position information of the voxel is quantized and coded to be quantization bits the number of which is more than the number of the allowed input bits for the actually-used DAC, which is equivalent to performing calculating by using a digital value with accuracy larger than actual accuracy of the DAC, so as to reduce a quantization error introduced when the spatial position information of the voxel is quantized and coded.

In a magnetic resonance imaging system, the number of the allowed input bits for the actually-used DAC is fixed and directly proportional to accuracy of the DAC. For example, it is assumed that the allowed input bits for the actually-used DAC are 20 bits, i.e., the DAC can perform D/A conversion for a digital value of 20 bits. In an example of the present disclosure, when the spatial position information of the voxel is quantized and coded, the spatial position information of the voxel is converted into a digital value of 24 bits. However, in fact, the DAC can only convert a digital value of 20 bits every time. When the aforementioned digital value of 24 bits is directly inputted into the DAC, it is in demand to discard 4 bits in the digital value of 24 bits so that the DAC can process the inputted digital value. Thus, the digital value inputted into the DAC is not accurate, and the gradient waveform outputted by the DAC is accordingly not accurate. Therefore, it should be considered how the digital value of 24 bits is converted into a digital value with bits which can be processed by the DAC.

At block S102, by starting from a highest bit of the first digital value, a higher-bit part of the first digital value is intercepted as the second digital value, wherein the intercepted part has the allowed input bits, and a quantization error is determined according to the first digital value and the second digital value.

The number of bits of the second digital value is same as that of the allowed input bits for the DAC, which is equivalent to directly converting the spatial position information of the voxel into a digital value of the actual allowed input bits for the DAC. For the spatial position information of a voxel, a quantization error may be generated between the process of converting the spatial position information into a first digital value of the preset quantization bits and the process of converting the spatial position information into a second digital value of the allowed input bits for the DAC. After the spatial position information of the voxel is quantized and coded to be the first digital value, the higher-bit part of the first digital value is intercepted to be the second digital value, the quantization error is a intercepted lower-bit part of the first digital value.

In this example, before the second digital value is inputted into the DAC, the following procedures are executed:

calculating a difference between the number of the preset quantization bits and the number of the allowed input bits for the DAC, in an example, the difference is equal to subtracting number of the allowed input bits for the DAC from the number of the preset quantization;

by starting from a lowest bit of the first digital value, intercepting a part of bits of the first digital value as the quantization error, where the number of bits of the intercepted part is equal to the difference.

Based on block S102, the first digital value, the quantization error and the second digital value in the present disclosure correspond to each other one to one.

For example, the allowed input bits for the DAC are 20 bits. A first digital value of 24 bits may be obtained by quantizing and coding the spatial position information of a voxel based on 24 bits. The difference between the number of bits of the first digital value and the number of the allowed input bits for the DAC is calculated to be 4. Then, 4 lowest bits of the first digital value are intercepted as the quantization error, and the 20 highest bits of the first digital value are intercepted as the second digital value. The second digital value may be equivalent to a digital value of 20 bits into which the spatial position information of the voxel is directly converted through quantizing and coding. Thus, the DAC can perform D/A conversion for the second digital value actually inputted.

If the quantization error is directly discarded, there is a large error for accuracy of a waveform actually outputted. Therefore, it may be considered to further process the second digital value, so as to improve the accuracy of the second digital value before the second digital value is inputted into the DAC, thereby enabling the DAC to output a high-accuracy waveform.

At block S103, the quantization error is accumulated to an error accumulation value, and the error accumulation value is compared with a carry digital value. If the error accumulation value is not less than the carry digital value, procedures in block S104 are executed; otherwise, procedures in block S105 are executed.

An order of accumulating respective quantization errors to the error accumulation value may be basically consistent with an order of quantizing and coding respective spatial position information corresponding to voxels, or may be basically consistent with an order of inputting second digital values into the DAC.

The carry digital value is a digital value which is carried from the error accumulation value to the lowest bit of the second digital value when the quantization error is accumulated to the error accumulation value. For example, it is assumed that the first digital value is 24 bits and the second digital value is 20 highest bits in the first digital value, and the quantization error is the 4 lowest bits in the first digital value. In this case, the carry digital value may be expressed as "10000", which is equivalent to adding 1 to the lowest bit of the second digital value. The output waveform of the DAC is a gradient waveform. Further, respective duration time periods of gradient waveforms may be basically same with each other, where the gradient waveforms correspond to respective spatial position information of voxels. That is, the DAC continuously outputs a gradient waveform corresponding to spatial position information of a voxel in a current duration time period, and the DAC continuously outputs a gradient waveform corresponding to spatial position information of another voxel in a next duration time period. Thus, the gradient waveform may be adjusted in a unified time period, e.g., the duration time period above is unified, so that the adjusted gradient waveform is more accurate.

Since a size of a gradient is calculated according to area of an output gradient waveform, when a gradient waveform corresponding to spatial position information of a voxel is adjusted, it is equivalent to adjusting amplitude of a gradient waveform outputted by the DAC, and may also be equivalent to adjusting a digital value inputted into the DAC.

When the error accumulation value reaches the carry digital value, the carry digital value is directly added to the second digital value corresponding to spatial position information of the current voxel.

At block S104, a third digital value is obtained by compensating the carry digital value to the second digital value corresponding to the spatial position information of the current voxel, which is taken as an input digital value for the DAC, and the error accumulation value is updated by subtracting the carry digital value from the error accumulation value.

At block S105, when the error accumulation value is less than the carry digital value, the error accumulation value is recorded as a basic value for accumulating a next quantization error, and the second digital value corresponding to the spatial position information of the current voxel is transmitted to the DAC, which is taken as an input digital value of the DAC.

The number of bits of the third digital value obtained by compensating the second digital value based on the error accumulation value is same as that of the actual allowed input bits for the DAC, thus, the third digital value can be converted into an analog to be outputted after a D/A conversion operation is executed. Thus, compared with directly inputting the second digital value not compensated into the DAC, the DAC can output a high-accuracy gradient waveform when the third digital value is inputted into the DAC.

Figure 2:
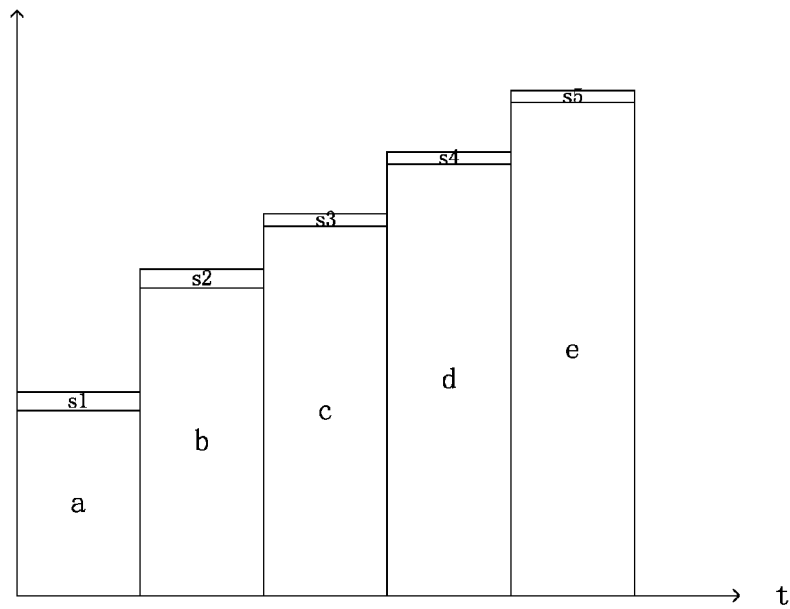
FIG. 2 is a schematic diagram illustrating a method of generating a gradient waveform according to an example of the present disclosure.

Referring to FIG. 2, in an example, it is assumed that a waveform containing 5 gradually-rising gradients is to be output, where the abscissa is output time t (unit: μs), and the ordinate is a gradient waveform amplitude, and each gradient corresponds to the spatial position information of a voxel. It is further assumed that respective spatial position information of voxels V1, V2, V3, V4 and V5 corresponding to the five gradient waveforms is quantized and coded according to preset quantization bits to obtain respective first digital values A, B, C, D and E, a duration time period of the gradient waveform corresponding to the spatial position information of each voxel is T (unit: μs). Accordingly, when each gradient waveform may be processed, it is equivalent to processing area of the gradient waveform.

If the spatial position information of the five voxels V1, V2, V3, V4 and V5 is quantized and coded by directly using the allowed input bits for the DAC, corresponding second digital values a, b, c, d and e may be obtained, respectively. The second digital values a, b, c, d and e may be less than the corresponding first digital values A, B, C, D and E, respectively, because the number of the allowed input bits for the DAC is less than the number of the preset quantization bits, thereby generating quantization errors.

By starting from a lowest bit, corresponding quantization errors s1, s2, s3, s4 and s5 may be obtained by intercepting a part of the first digital values A, B, C, D and E, where the number of the intercepted part is equal to a difference (the difference is determined by subtracting the number of the allowed input bits for the DAC from the number of the preset quantization bits). Further, corresponding second digital values a, b, c, d and e may be obtained by discarding the quantization errors s1, s2, s3, s4 and s5 from the corresponding first digital values A, B, C, D and E, respectively, i.e., a=A−s1, b=B−s2, c=C−s3, d=D−s4, and e=E−s5.

Next, according to an order of quantizing and coding the respective spatial position information of the voxels V1, V2, V3, V4 and V5, the quantization errors s1, s2, s3, s4 and s5 may be sequentially accumulated. For example, as shown in FIG. 3, the quantization errors s1 and s2 are accumulated, which is equivalent to accumulating areas of gradient waveforms corresponding to the quantization errors s1 and s2.

Figures 3, 4, 5:
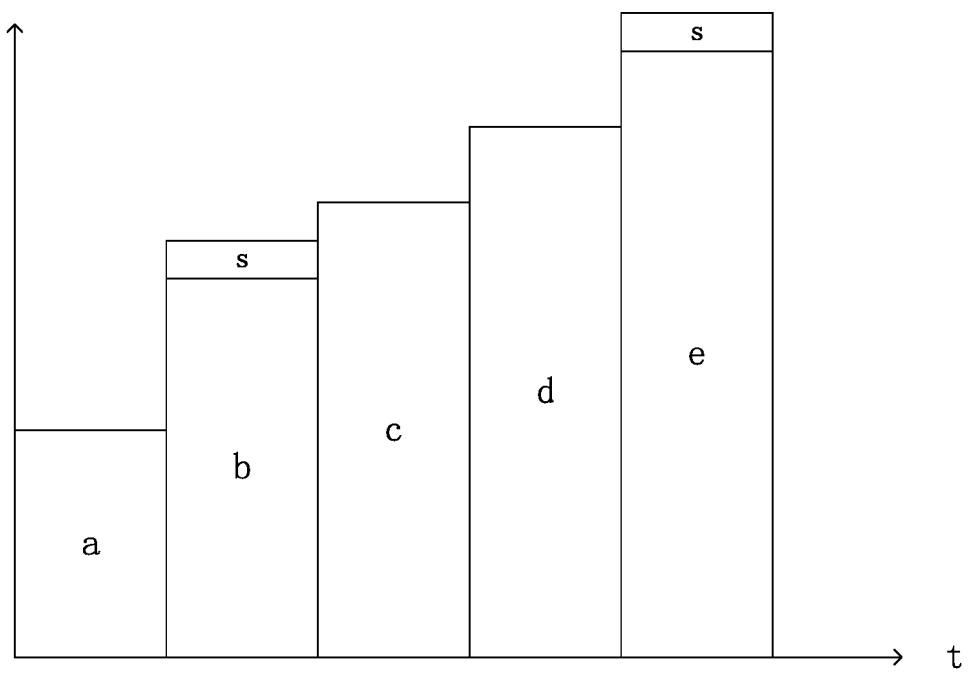
FIG. 3 is a schematic diagram illustrating a process of accumulating quantization errors of a first gradient and a second gradient in FIG. 2 according to example of the present disclosure.
FIG. 4 is a schematic diagram illustrating a process of accumulating quantization errors of a third gradient to a fifth gradient in FIG. 2 according to example of the present disclosure.
FIG. 5 is a schematic diagram illustrating a compensated output gradient waveform according to an example of the present disclosure.

As shown in FIG. 3, it is assumed that an error accumulation value W is obtained, which is equal to (s1+s2), i.e., (s+r1), where s is a carry digital value, and r1 is a residual value obtained by subtracting the carry digital value s from the error accumulation value W, which may be taken as a new error accumulation value W for accumulating the next quantization error s3.

According to an example in the present disclosure, output accuracy of a DAC may be equivalent to area of a unit of a gradient waveform amplitude in a duration time period. For example, the output accuracy of the DAC is obtained by multiplying a unit of gradient waveform amplitude with the duration time period. A digital value to be inputted into the DAC can be added with 1 based on the carry digital value, which is equivalent to adding output accuracy to the area of the gradient waveform outputted by the DAC.

Since the error accumulation value W is more than the carry digital value, the carry digital value s may be added to the second digital value b corresponding to the current voxel V2, which is equivalent to adjusting the output value of the second gradient waveform corresponding to the current voxel V2 to be (b+1)*T, and the quantization error corresponding to a subsequent voxel is accumulated to a residual error accumulation value r1.

As shown in FIG. 4, a new error accumulation value W may be obtained by sequentially accumulating the quantization errors s3, s4 and s5 to the error accumulation value r1, i.e., W=r1+s3+s4+s5=s+r2, where r2 is a final error corresponding to the five gradient waveforms.

An output value of the fifth gradient waveform corresponding to the current voxel V5 may be adjusted to be (e+1)*T by accumulating the carry digital value s to the second digital value e of the current voxel V5.

It can be seen from above that, the digital values to be inputted into the DAC corresponding to five voxels are adjusted according to an accumulation method, which is equivalent to adjusting the gradient waveform outputted by the DAC. The adjusted gradient waveform is as shown in FIG. 5. The quantization errors corresponding to the processed voxels are sequentially accumulated, the digital values inputted into the DAC are compensated when the error accumulation value reaches the carry digital value, thus, the final error of the gradient waveform outputted by the DAC can be effectively reduced, thereby improving output waveform accuracy of the DAC.

In an example, if there are more gradient waveforms to be outputted after the fifth gradient waveform, quantization error accumulation may be continuously performed based on the current error accumulation value r2 until the gradient waveforms corresponding to all voxels are completely processed.

According to a method of generating a gradient waveform provided in the present disclosure, the spatial position information of voxels is converted into the digital value the number of bits of which is large (more than the number of allowed input bits for the DAC) and quantization errors generated in the conversion process are accumulated and compensated. In this way, compared with directly converting the spatial position information of the voxels into digital values of the allowed input bits for the DAC, an overall error of the digital values finally inputted into the DAC is smaller, so that output waveform accuracy of the DAC may be improved in a case without changing the allowed input bits for the DAC. That is, a low-accuracy DAC can be enabled to achieve reach accuracy of a high-accuracy DAC.

Figure 6:
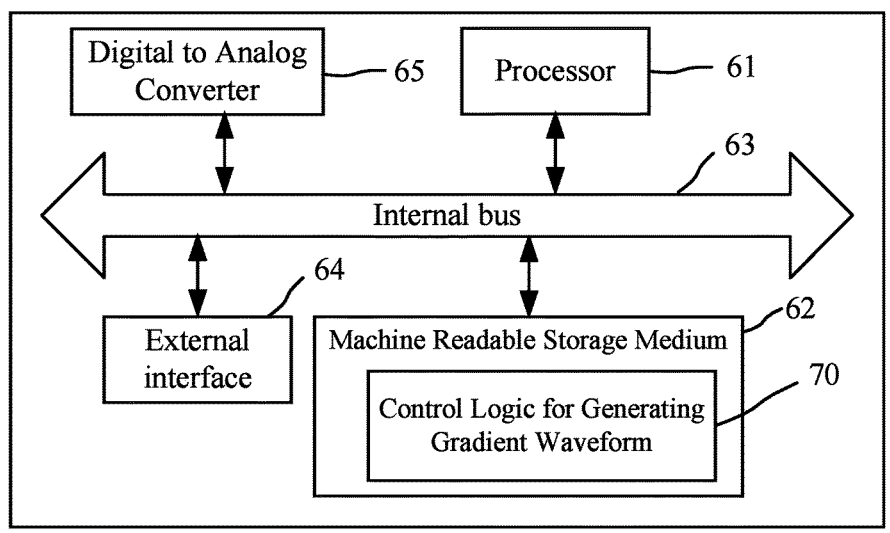
FIG. 6 is a schematic diagram illustrating a hardware structure of a gradient waveform generator according to an example of the present disclosure.

As shown in FIG. 6, corresponding to the methods above, the present disclosure further provides a gradient waveform generator. As shown in FIG. 6, the generator includes: a processor 61, a machine readable storage medium 62 and a digital to analog converter, where the processor 61 and the machine readable storage medium 62 are interconnected via an internal bus 63. In another possible implementing method, the generator may further include an external interface 64 so as to communicate with other devices or components.

In examples, the machine readable storage medium 62 may be: a Read-Only Memory (ROM), a volatile memory, a non-volatile memory, a flash memory, a storage drive (e.g. hard disk drive), a solid state hard disk, any type of storage disk (e.g., optical disk, Digital Video Disk (DVD)), or a similar storage medium, or a combination thereof.

Figure 7:
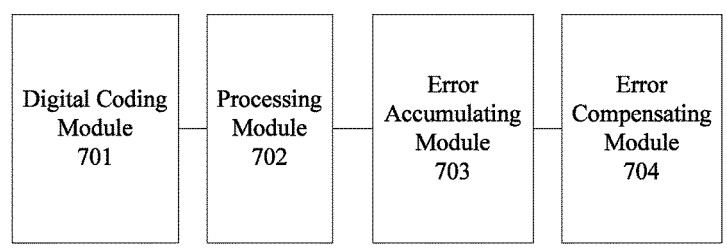
FIG. 7 is a schematic diagram illustrating functional blocks of a logic of generating a gradient waveform according to an example of the present disclosure.

Further, the machine readable storage medium 62 stores the control logic 60 for generating a gradient waveform. As shown in FIG. 7, functionally, the control logic includes modules as follows.

A digital coding module 701 is configured to obtain a first digital value by quantizing and coding spatial position information of a voxel of a subject according to the number of preset quantization bits, wherein the number of the quantization bits are more than the number of allowed input bits for a Digital to Analog Converter (DAC).

A processing module 702 is configured to determine a second digital value to be inputted into the DAC according to the first digital value and the number of the allowed input bits for the DAC; determine a quantization error according to the first digital value and the second digital value.

An error accumulating module 703 is configured to update an error accumulating value by accumulating the quantization error to the error accumulation value, wherein the error accumulating value indicates an error corresponding to voxels of the subject which have been processed.

An error compensating module 704 configured to correct the second digital value according to the error accumulation value; input the corrected second digital value into the DAC in a way that the DAC outputs a gradient waveform according to the corrected second digital value inputted.

In an example, the processing module 702 is configured to:
  by starting from a highest bit of the first digital value, intercept a part of the first digital value as the second digital value, wherein the intercepted part has the allowed input bits.

In an example, the processing module 702 is configured to:
  determine a difference between the number of the quantization bits and the number of the allowed input bits for the DAC;
  by starting from a lowest bit of the first digital value, intercept a part of the first digital value as the quantization error, wherein the number of bits of the intercepted part is equal to the difference.

In an example, the error accumulating module 703 is configured to compare the error accumulation value with a carry digital value of the DAC, wherein the carry digital value corresponds to a unit of a gradient waveform amplitude for the gradient waveform outputted by the DAC; when the error accumulation value is not less than the carry digital value, correct the second digital value by adding 1 to the second digital value, update the error accumulation value by subtracting the carry digital value from the error accumulation value; when the error accumulation value is less than the carry digital value, maintain the second digital value and the error accumulation value.

In an example, the digital coding module 701, respective duration time periods of gradient waveforms are same with each other, wherein the gradient waveforms corresponds to respective spatial position information of a plurality of voxels of the subject.

In an example, for the error accumulating module 703, an order of accumulating quantization errors corresponding to a plurality of voxels to the error accumulation value is same as an order of quantizing and coding respective spatial position information of the voxels.

Taking software implementation as an example to further describe how the gradient waveform generator executes the control logic 70. In the example, the control logic 70 can be interpreted as computer instructions stored on the machine readable storage medium 62. When a CPU 61 of the gradient waveform generator in the present disclosure executes the control logic 70, the CPU 61 executes operations as follows by invoking instructions corresponding to the control logic 70 and stored on the machine readable storage medium 62:
  obtain a first digital value by quantizing and coding spatial position information of a voxel of a subject according to the number of preset quantization bits, wherein the number of the quantization bits are more than the number of allowed input bits for a Digital to Analog Converter (DAC);
  determine a second digital value to be inputted into the DAC according to the first digital value and the number of the allowed input bits for the DAC;
  determine a quantization error according to the first digital value and the second digital value;
  update an error accumulating value by accumulating the quantization error to the error accumulation value, wherein the error accumulating value indicates an error corresponding to voxels of the subject which have been processed;
  correct the second digital value according to the error accumulation value; and
  input the corrected second digital value into the DAC in a way that the DAC outputs a gradient waveform according to the corrected second digital value inputted.

In an example, when determining the second digital value to be inputted into the DAC, the processor is caused by the machine-executable instructions corresponding to the control logic and stored on the machine readable storage medium to:
  by starting from a highest bit of the first digital value, intercept a part of the first digital value as the second digital value, wherein the intercepted part has the allowed input bits.

In an example, when determining the quantization error, the processor is caused by the machine-executable instructions corresponding to the control logic of generating a gradient waveform and stored on the machine readable storage medium to:

determine a difference between the number of the quantization bits and the number of the allowed input bits for the DAC;

by starting from a lowest bit of the first digital value, intercept a part of the first digital value as the quantization error, wherein the number of bits of the intercepted part is equal to the difference.

In an example, when correcting the second digital value according to the error accumulation value, the processor is caused by the machine-executable instructions corresponding to the control logic and stored on the machine readable storage medium to:

compare the error accumulation value with a carry digital value of the DAC, wherein the carry digital value corresponds to a unit of a gradient waveform amplitude for the gradient waveform outputted by the DAC;

when the error accumulation value is not less than the carry digital value, correct the second digital value by adding 1 to the second digital value;

update the error accumulation value by subtracting the carry digital value from the error accumulation value; and when the error accumulation value is less than the carry digital value, maintain the second digital value and the error accumulation value.

In an example, respective duration time periods of gradient waveforms are same with each other, wherein the gradient waveforms corresponds to respective spatial position information of a plurality of voxels of the subject.

In an example, the generator according to claim 7, wherein an order of accumulating quantization errors corresponding to a plurality of voxels to the error accumulation value is same as an order of quantizing and coding respective spatial position information of the voxels.

Figure 8:
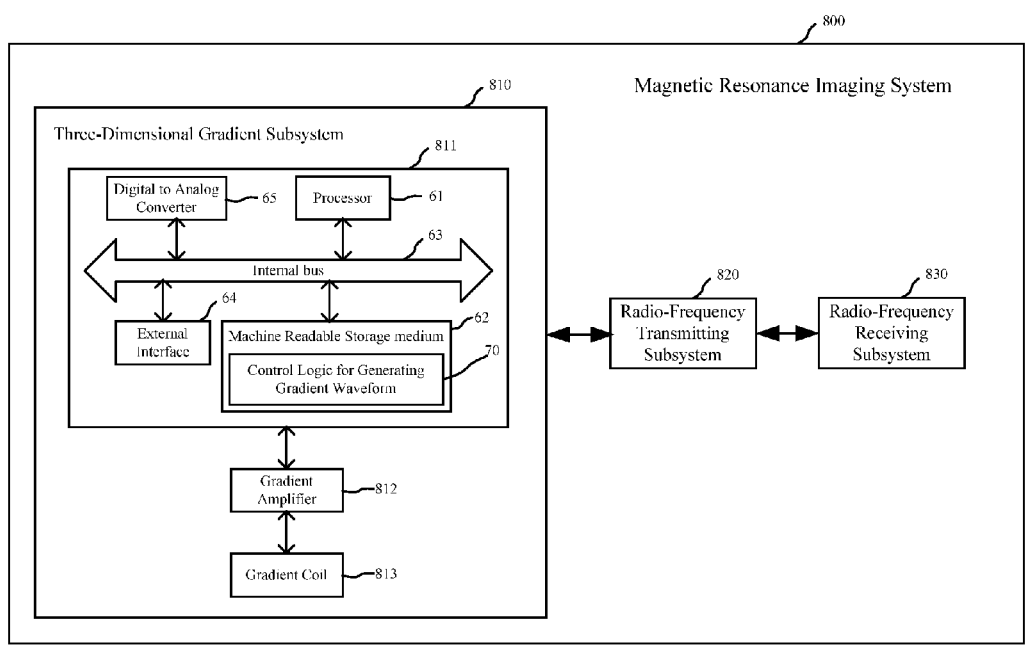
FIG. 8 is a schematic diagram illustrating a hardware structure of a magnetic resonance imaging system according to an example of the present disclosure.

Corresponding to the methods above, the present disclosure further provides a nuclear magnetic resonance imaging system. FIG. 8 is a schematic diagram illustrating a structure of a nuclear magnetic resonance imaging system according to an example of the present disclosure. As shown in FIG. 8, the magnetic resonance system 800 includes a three-dimensional gradient subsystem 810, a radio-frequency transmitting subsystem 820, and a radio-frequency receiving subsystem 830.

The three-dimensional gradient subsystem 810 includes a gradient waveform generator 811, a gradient amplifier 812, and a gradient coil 813. The gradient waveform generator 811 is configured to generate three-dimensional gradient pulse signals, where the three-dimensional gradient pulse signals include a slice-selection direction gradient signal, a frequency-coding gradient signal, and a phase-coding gradient signal. The gradient amplifier 812 is configured to amplify the three-dimensional gradient pulse signals. And the gradient coil 813 is configured to generate a three-dimensional gradient magnetic field based on the three-dimensional gradient pulse signals, where the three dimensional gradient magnetic field enables an image to have spatial information.

The gradient waveform generator 811 includes a processor 61, a machine readable storage medium 62 and a digital to analog converter as shown in FIG. 6, where the processor 61 and the machine readable storage medium 62 are interconnected via an internal bus 63. In another possible implementing method, the gradient waveform generator 811 may further include an external interface 64 so as to communicate with other devices or components.

The machine readable storage medium 62 stores a control logic 60 for generating a gradient waveform. A manner of executing the control logic 70 by the gradient waveform generator is same as that in the examples above, which is not redundantly described herein.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

The invention claimed is:

1. A method of generating a gradient waveform, comprising:

obtaining a first digital value by quantizing and coding spatial position information of a voxel of a subject according to the number of preset quantization bits, wherein the number of the quantization bits are more than the number of allowed input bits for a Digital to Analog Converter (DAC);

determining a second digital value to be inputted into the DAC according to the first digital value and the number of the allowed input bits for the DAC;

determining a quantization error according to the first digital value and the second digital value;

updating an error accumulating value by accumulating the quantization error to the error accumulation value, wherein the error accumulating value indicates an error corresponding to voxels of the subject which have been processed;

correcting the second digital value according to the error accumulation value; and inputting the corrected second digital value into the DAC in a way that the DAC outputs a gradient waveform according to the corrected second digital value inputted.

2. The method according to claim 1, wherein determining the second digital value to be inputted into the DAC comprises:

by starting from a highest bit of the first digital value, intercepting a part of the first digital value as the second digital value, wherein the intercepted part has the allowed input bits.

3. The method according to claim 1, wherein determining the quantization error comprises:
determining a difference between the number of the quantization bits and the number of the allowed input bits for the DAC;
by starting from a lowest bit of the first digital value, intercepting a part of the first digital value as the quantization error, wherein the number of bits of the intercepted part is equal to the difference.

4. The method according to claim 1, wherein correcting the second digital value according to the error accumulation value comprises:
comparing the error accumulation value with a carry digital value of the DAC, wherein the carry digital value corresponds to a unit of a gradient waveform amplitude for the gradient waveform outputted by the DAC;
when the error accumulation value is not less than the carry digital value,
correcting the second digital value by adding 1 to the second digital value;
updating the error accumulation value by subtracting the carry digital value from the error accumulation value; and
when the error accumulation value is less than the carry digital value,
maintaining the second digital value and the error accumulation value.

5. The method according to claim 1, wherein respective duration time periods of gradient waveforms are same with each other, wherein the gradient waveforms corresponds to respective spatial position information of a plurality of voxels of the subject.

6. The method according to claim 1, wherein an order of accumulating quantization errors corresponding to a plurality of voxels to the error accumulation value is same as an order of quantizing and coding respective spatial position information of the voxels.

7. A gradient waveform generator, comprising:
a Digital to Analog Converter (DAC),
a processor,
a non-transitory machine-readable storage medium storing machine executable instructions which are executable by the processor to:
obtain a first digital value by quantizing and coding spatial position information of a voxel of a subject according to the number of preset quantization bits, wherein the number of the quantization bits are more than the number of allowed input bits for a Digital to Analog Converter (DAC);
determine a second digital value to be inputted into the DAC according to the first digital value and the number of the allowed input bits for the DAC;
determine a quantization error according to the first digital value and the second digital value;
update an error accumulating value by accumulating the quantization error to the error accumulation value, wherein the error accumulating value indicates an error corresponding to voxels of the subject which have been processed;
correct the second digital value according to the error accumulation value; and
input the corrected second digital value into the DAC in a way that the DAC outputs a gradient waveform according to the corrected second digital value inputted.

8. The generator according to claim 7, wherein the processor is caused by the machine-executable instructions to:
by starting from a highest bit of the first digital value, intercept a part of the first digital value as the second digital value, wherein the intercepted part has the allowed input bits.

9. The generator according to claim 7, wherein the processor is caused by the machine executable instructions to:
determine a difference between the number of the quantization bits and the number of the allowed input bits for the DAC;
by starting from a lowest bit of the first digital value, intercept a part of the first digital value as the quantization error, wherein the number of bits of the intercepted part is equal to the difference.

10. The generator according to claim 7, wherein the processor is caused by the machine executable instructions to:
compare the error accumulation value with a carry digital value of the DAC, wherein the carry digital value corresponds to a unit of a gradient waveform amplitude for the gradient waveform outputted by the DAC;
when the error accumulation value is not less than the carry digital value,
correct the second digital value by adding 1 to the second digital value;
update the error accumulation value by subtracting the carry digital value from the error accumulation value; and
when the error accumulation value is less than the carry digital value,
maintain the second digital value and the error accumulation value.

11. The generator according to claim 7, wherein respective duration time periods of gradient waveforms are same with each other, wherein the gradient waveforms corresponds to respective spatial position information of a plurality of voxels of the subject.

12. The generator according to claim 7, wherein an order of accumulating quantization errors corresponding to a plurality of voxels to the error accumulation value is same as an order of quantizing and coding respective spatial position information of the voxels.

13. A magnetic resonance imaging system, comprising a three-dimensional gradient subsystem configured to provide a gradient magnetic field, wherein
the three-dimensional gradient subsystem comprises a gradient waveform generator,
the gradient waveform generator comprises:
a Digital to Analog Converter (DAC),
a processor,
a non-transitory machine-readable storage medium storing machine executable instructions which are executable by the processor to:
obtain a first digital value by quantizing and coding spatial position information of a voxel of a subject according to the number of preset quantization bits, wherein the number of the quantization bits are more than the number of allowed input bits for a Digital to Analog Converter (DAC);
determine a second digital value to be inputted into the DAC according to the first digital value and the number of the allowed input bits for the DAC;

determine a quantization error according to the first digital value and the second digital value;

update an error accumulating value by accumulating the quantization error to the error accumulation value, wherein the error accumulating value indicates an error corresponding to voxels of the subject which have been processed;

correct the second digital value according to the error accumulation value; and input the corrected second digital value into the DAC in a way that the DAC outputs a gradient waveform according to the corrected second digital value inputted.

14. The system according to claim 13, wherein the processor is caused by the machine-executable instructions to:

by starting from a highest bit of the first digital value, intercept a part of the first digital value as the second digital value, wherein the intercepted part has the allowed input bits.

15. The system according to claim 13, wherein the processor is caused by the machine executable instructions to:

determine a difference between the number of the quantization bits and the number of the allowed input bits for the DAC;

by starting from a lowest bit of the first digital value, intercept a part of the first digital value as the quantization error, wherein the number of bits of the intercepted part is equal to the difference.

16. The system according to claim 13, wherein the processor is caused by the machine executable instructions to:

compare the error accumulation value with a carry digital value of the DAC, wherein the carry digital value corresponds to a unit of a gradient waveform amplitude for the gradient waveform outputted by the DAC;

when the error accumulation value is not less than the carry digital value, correct the second digital value by adding 1 to the second digital value;

update the error accumulation value by subtracting the carry digital value from the error accumulation value; and when the error accumulation value is less than the carry digital value, maintain the second digital value and the error accumulation value.

17. The system according to claim 13, wherein respective duration time periods of gradient waveforms are same with each other, wherein the gradient waveforms corresponds to respective spatial position information of a plurality of voxels of the subject.

18. The system according to claim 13, wherein an order of accumulating quantization errors corresponding to a plurality of voxels to the error accumulation value is same as an order of quantizing and coding respective spatial position information of the voxels.

* * * * *